United States Patent [19]
Evans

[11] Patent Number: 5,503,150
[45] Date of Patent: Apr. 2, 1996

[54] APPARATUS AND METHOD FOR NONINVASIVE MICROWAVE HEATING OF TISSUE

[75] Inventor: Gary E. Evans, Hanover, Md.

[73] Assignee: Westinghouse Electric Corp., Pittsburgh, Pa.

[21] Appl. No.: 208,553

[22] Filed: Mar. 10, 1994

[51] Int. Cl.$^6$ ...................................................... A61B 5/00
[52] U.S. Cl. ........................ 128/653.1; 607/101; 607/102
[58] Field of Search ............................ 607/96–102, 154, 607/156; 128/653.1, 660.03, 736

[56] References Cited

U.S. PATENT DOCUMENTS

| | | |
|---|---|---|
| 4,346,716 | 8/1982 | Carr . |
| 4,403,618 | 9/1983 | Turner et al. . |
| 4,448,198 | 5/1984 | Turner . |
| 4,462,412 | 7/1984 | Turner . |
| 4,589,423 | 5/1986 | Turner . |
| 4,638,813 | 1/1987 | Turner . |
| 4,658,836 | 4/1987 | Turner . |
| 4,669,475 | 6/1987 | Turner . |
| 4,672,980 | 6/1987 | Turner . |
| 4,712,559 | 12/1987 | Turner . |
| 4,774,961 | 10/1988 | Carr . |
| 4,798,215 | 1/1989 | Turner ................................. 607/102 |
| 4,815,479 | 3/1989 | Carr ................................... 607/102 |
| 4,860,752 | 8/1989 | Turner . |
| 4,974,587 | 12/1990 | Turner et al. ........................ 607/101 |
| 5,097,844 | 3/1992 | Turner . |
| 5,220,927 | 6/1993 | Astrahan et al. . |

Primary Examiner—Ruth S. Smith

[57] ABSTRACT

A method and apparatus for noninvasively locating and heating a volume of tissue, specifically a cancerous tumor, including placing a bolus in contact with the patient and substantially around an area of interest including the volume of tissue, placing an array of antennas on the bolus and substantially around the area of interest, imaging the area of interest, selecting an approximate center of the volume of tissue on said initial image, determining appropriate amplitudes and phases for the antennas, energizing each element at respective appropriate amplitudes and phases to heat the volume of tissue, repetitively imaging the area of interest to create subsequent images, and subtracting said initial image from the subsequent images to determine temperature changes in the area of interest.

16 Claims, 8 Drawing Sheets

APPARATUS AND METHOD FOR NONINVASIVE MICROWAVE HEATING OF TISSUE

BACKGROUND OF THE INVENTION

1. Field of the Invention

The present invention relates in general to an apparatus and method for noninvasively locating and heating tissue. More particularly, the present invention relates to an apparatus and associated method for noninvasively locating and heating a volume of tissue, including the ability to detect temperature changes in the volume of tissue.

It is generally recognized that the use of microwave energy to produce moderate internal heating is an effective tool in the treatment of tissue, especially cancerous tumors. The primary factor limiting such treatment in the past has been the difficulty of delivering the heat to a target region below the skin surface. Of course, it is possible to use an interstitial source, but this method has the drawback of being invasive. Because of this limitation, noninvasive treatment to date has largely been confined to treatment of surface tumors since it is difficult to heat deep tumors without also heating the intervening tissue.

In order to get significant heating in tumors more than a few millimeters below the skin surface, the field from a single source at the skin surface will have to be high and therefore painful. One approach has used a moving source, generally achieved by switching discrete sub-arrays of sources. However, the moving source results in an incoherent summation of energy at the tumor site. While tending to reduce the heating effects in the intervening tissue, this method has not eliminated the heating of the intervening tissue or reduced it to an acceptable level.

Additionally, to insure that the desired volume of tissue is preferentially heated, an operator must not only know the characteristics in the area of interest but also be able to determine which tissues are being heated. Currently, the ability to make this determination depends on the use of an interstitial probe or a radiometer. The current methods also do not allow for imaging of the area, except to use other modalities: CT, MRI, ultrasound, etc. Such methods, while noninvasive, do not provide appropriate characteristics of the area and tissue to maximize the heating of the target tissue with microwaves.

SUMMARY OF THE INVENTION

Accordingly, the present invention is directed to an apparatus and corresponding method that substantially obviate one or more of the problems due to the limitations and disadvantages of the related art. Additional features and advantages of the invention will be set forth in the description which follows, and in part will be apparent from the description, or may be learned by practice of the invention. The objectives and other advantages of the invention will be realized and attained by the apparatus and corresponding process particularly pointed out in the written descriptions and claims hereof, as well as in the appended drawings.

To achieve these and other advantages in accordance with the purpose of the invention, as embodied and broadly described the invention includes a bolus, the bolus being in contact with the patient substantially surrounding an area of interest which includes a volume of tissue, an array of antennas on the bolus and also surrounding the area of interest, the array includes a plurality of elements which are independently operable and have the ability to send and receive signals, means for selectively energizing at least one of the elements to send signals, means for selectively energizing at least one other element to receive the signals, means for determining dielectric constants within the area of interest to obtain a configuration of measured dielectric constants from the received signals, means for generating an initial image based upon the configuration of the measured dielectric constants, means for selecting an approximate center of the volume of tissue on the initial image, means for determining appropriate amplitude and phases for each of the elements in accordance with the configuration of measured dielectric constants, and means for energizing each element of the array at appropriate amplitudes and phases to focus the energy in approximate center of the volume of tissue to preferentially heat the volume of tissue.

In another aspect, the invention includes a method for noninvasively locating and heating a volume of tissue which includes the steps of placing a bolus in contact with the patient and substantially around an area of interest, the area of interest include the volume of tissue, placing an array of antennas on the bolus and substantially around the area of interest, the array includes a plurality of independently operable elements having the ability to send and receive signals, selectively energizing at least one element to send signals, selectively energizing at least one other element to receive the signals, determining dielectric constants at a plurality of locations in said area of interest to obtain a configuration of measured dielectric constants from said received signals, generating an initial image based upon the configuration of said measured dielectric constants, selecting an approximate center of the volume of-tissue on said initial image, determining appropriate amplitudes and phases for each one of the elements in accordance with the configuration of measured dielectric constants, and energizing each element at respective appropriate amplitudes and phases to focus energy in the approximate center of the volume of tissue to preferentially heat the volume of tissue.

It is to be understood that both the foregoing general description and the following detailed description are exemplary and explanatory and are intended to provide further explanation of the invention as claimed. The accompanying drawings are included to provide a further understanding of the invention and are incorporated in and constitute a part of the specification, illustrate one embodiment of the invention, and together with the description serve to explain the principles of the invention.

BRIEF DESCRIPTION OF THE DRAWINGS

The accompanying drawings, which are incorporated in and constitute a part of the specification, illustrate a presently preferred embodiment and method of the invention and, together with the general description given above and the detailed description of the preferred embodiment given below, serve to explain the principles of the invention. Of the drawings.

DETAILED DESCRIPTION OF THE PREFERRED EMBODIMENT

Figure 1:
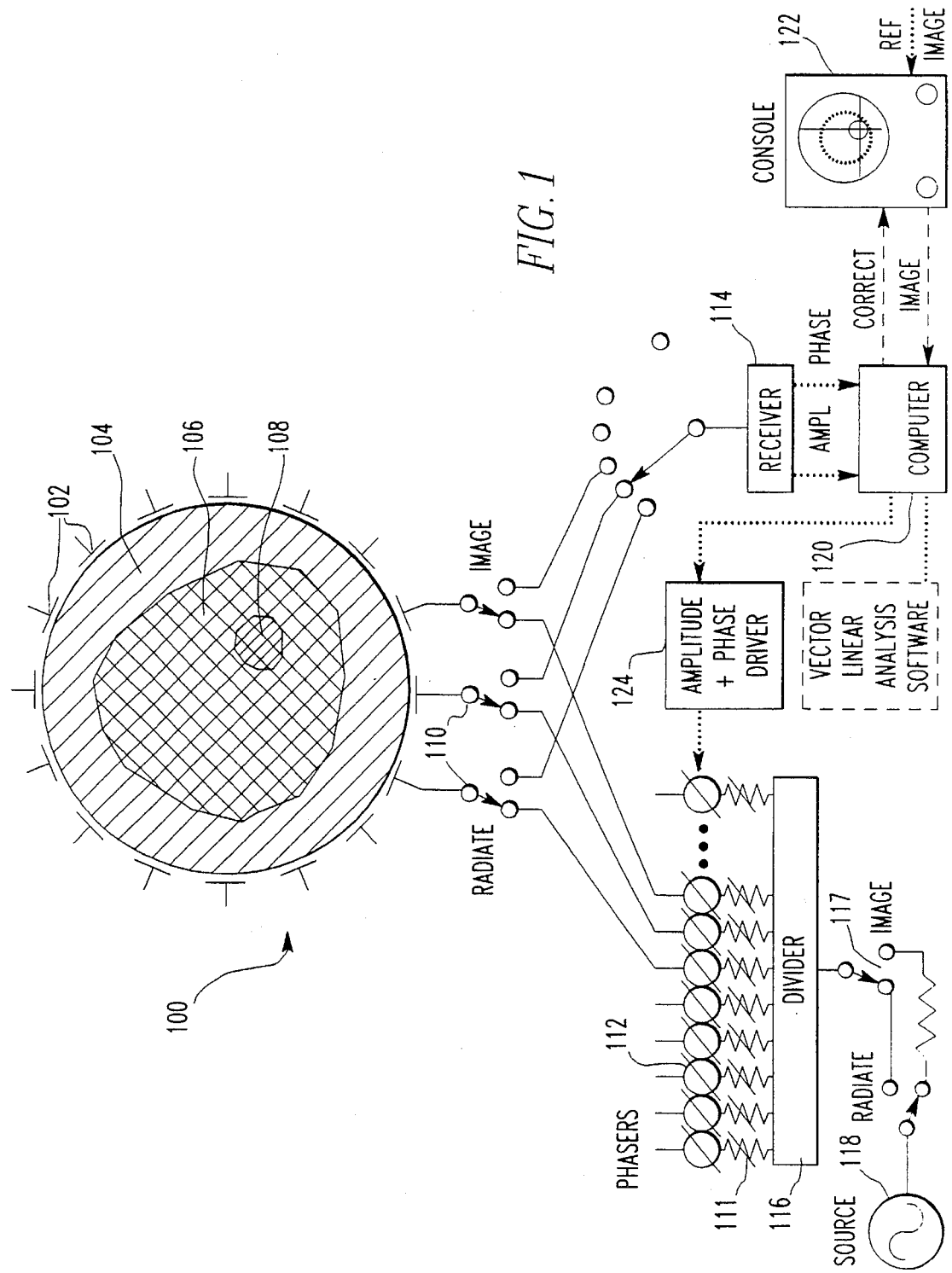
FIG. 1 schematically illustrates one embodiment of the present invention.

Reference will now be made in detail to the presently preferred embodiments of the invention as illustrated in the accompanying drawings. An exemplary embodiment of the apparatus is shown in FIG. 1 and is designated generally by reference numeral 100. Apparatus 100 includes a plurality of antenna 102 placed on a bolus 104, which is in turn placed in intimate contact with an area of interest 106 of a patient (not shown) including a volume of tissue to be heated 108. The antennas 102 are coupled via switches 110 to either attenuators 111 and phasers 112 or to receiver 114. Source 118 is coupled through the radiate/image switches 117, divider 116, phasers 112, and switches 110 to the array elements 102. Receiver 114, which detects the amplitude and phase of signals received through antennas 102, is connected to the computer 120 which includes a console 122 for viewing images and a keyboard or other operator input (not shown). Computer 120 is also connected to an amplitude and phase driver 124 which is in turn coupled to the attenuators 111 and phasers 112 to set the correct phase and amplitude values in order to either heat the volume of tissue or image the area of interest 106.

Figure 1A:
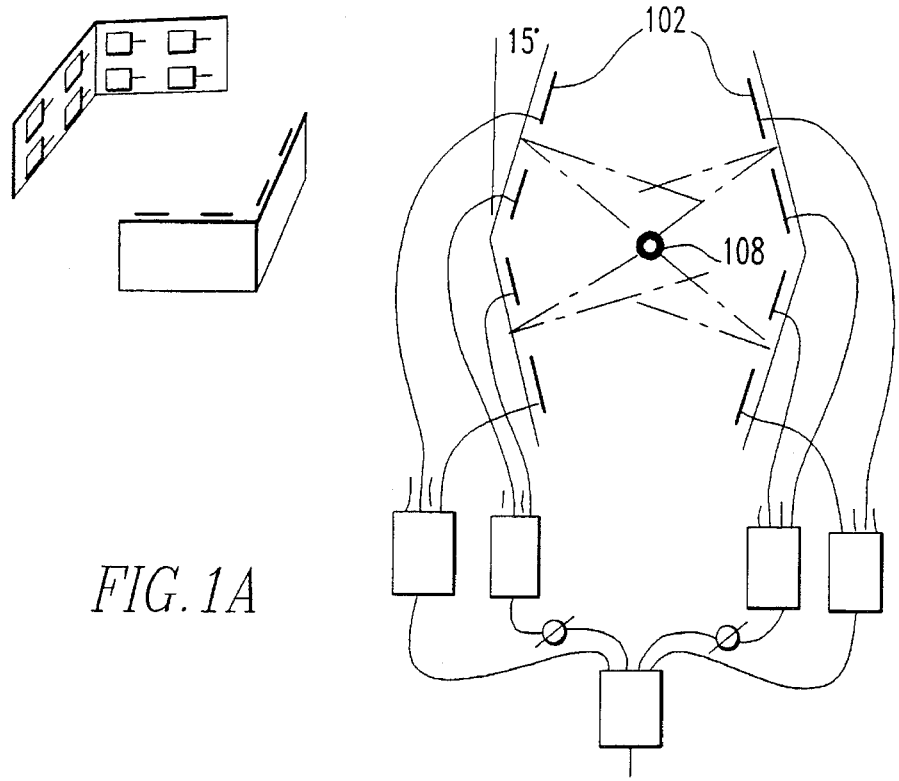
FIGS. 1a and 1b schematically illustrate other embodiments of the present invention.
Figure 1B:
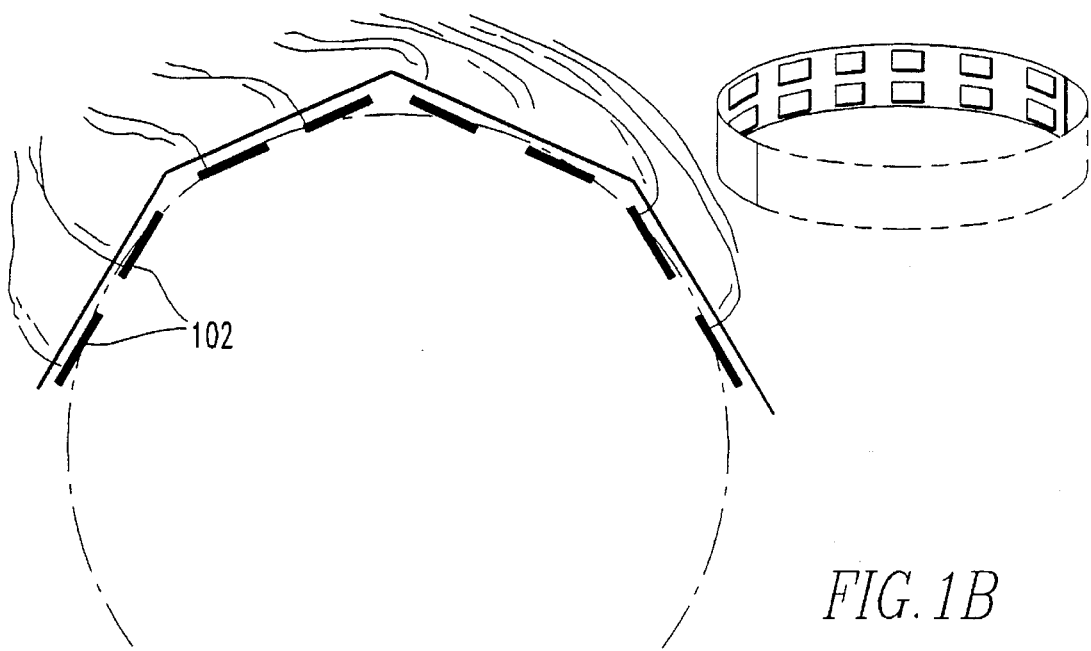

The antenna elements 102 can be any type of microwave radiator as long as it is reciprocal (e.g., also a receiver), i.e., a patch, a dipole, a slot or a horn. They must be spaced close enough (i.e., a half wavelength in the bolus material) so as to produce only one maximum field point. The antenna array must also be able to send and receive signals at a plurality of frequencies. Array elements 102 are preferentially set up in a cylindrical array geometry around the area of interest 106, as shown in FIG. 1. However, depending upon the area of interest of the patient, a polygonal array, a semicircular array, or even a planar array may be preferred, or required due to physical limitations. For example, FIG. 1a shows a second embodiment of the apparatus with the plurality of antenna arranged in a polygonal array. Similarly, FIG. 1b, a third embodiment of the apparatus, illustrates the plurality of antenna arranged in a semicircular array. In both of these embodiments, the remaining apparatus would be the same or substantially similar as for the embodiment of apparatus 100.

Bolus 104 is used to even out the surface of the patient (not shown), reduce the radiator size, and reduce reflections at the tissue surface, as well as to make the determinations of the dielectric constant, more accurate and to focus the microwave energy more locally. While it is preferable that bolus 104 be of a type that allows fluid to circulate through it, it is not necessary. A bolus with circulating liquid also aids in removing heat from the skin surface, thereby allowing a larger input signal.

Switches 110 are preferably of the diode type (i.e., PIN diodes) for rapid, low loss switching at moderate power. The other elements of apparatus 100 include a driver 124 to bias the switch elements, a receiver 114 to convert the microwave signals to digital amplitude and phase readings, a computer 120 to perform the imaging calculations and a console 122 to display the results and to interact with the operator.

In using the embodiment of FIG. 1 to noninvasively image the area of interest 106 and heat the volume of tissue 108, the bolus 104 and an array of antennas 102 are placed around the area of interest 106. Then computer 120 drives the attenuators 111 and phasers 112 through amplitude and phase driver 124 to set the appropriate amplitudes and phases of the elements 102 for imaging. Source 118 sends a signal through switches 117 to the divider 116, phasers 112, and switches 110 to each of the elements 102. While imaging, each of the switches 110 is successively set to radiate, while any number of the remaining elements 102 are switched to receive the signals sent by the element 102. Usually only one element is energized to send signals and all of the other elements 102 are set to receive signals. Typically, when imaging the area of interest 106, the source frequency can be greater than 800 Mhz or the same as when heating, approximately 915 MHz. While the use of the 915 MHz frequency is preferable for heating, a higher frequency, on the order of 3000 MHz, allows for better resolution in an image. Such high frequencies are not as preferable for heating because signal loss in the tissue is too high. Therefore, during heating, the frequency of source 118 should be set less than 1000 Mhz and preferably set around 915 MHz.

Once the signals have been received by computer 120 through receiver 114, the computer 120 then determines the dielectric constants at a plurality of locations in the area of interest in order to obtain a configuration of measured dielectric constants to generate an image. Such a determination is shown in the flow charts of FIGS. 3 and 4.

Figure 3:
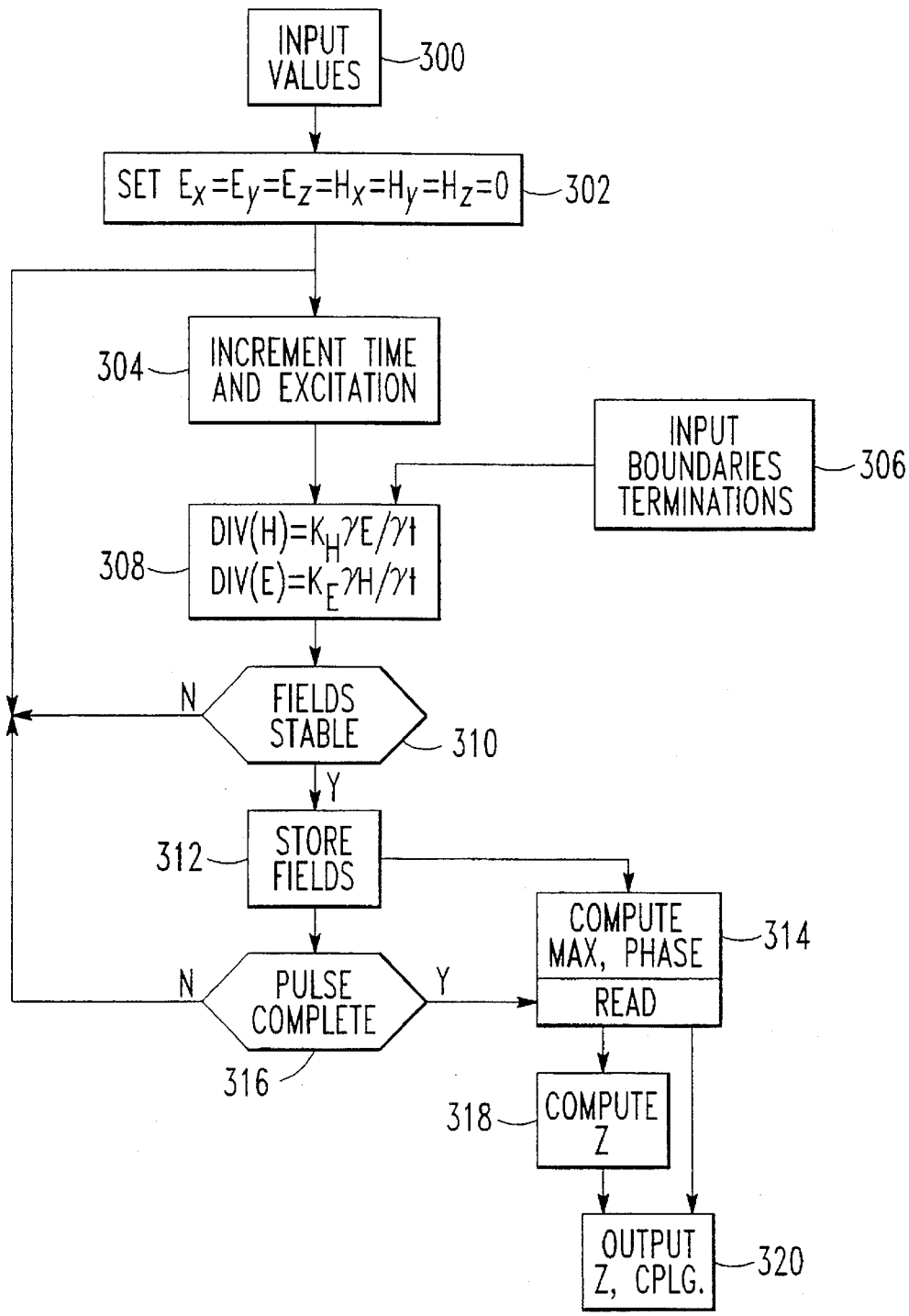
FIG. 3 is a flow chart illustrating the determination of coupling values in accordance with an embodiment of the present invention.

At step 300 of FIG. 3, initial estimates of the source signal frequency and pulse shape are input. As discussed above, for imaging this would be either around 3000 MHz for high definition, or at 915 MHz to duplicate heating conditions, but other frequencies can be used. The operator also inputs the grid size or pixel size of the image as well as boundaries and terminations 306 of the area of interest, excitations and initial estimates of the real and imaginary parts of the dielectric constant, $\epsilon_r'$ and $\epsilon_r''$. These estimates are preferably determined by imaging the area of interest by a more conventional modality. Those modalities include CT, MRI, sonograms, nuclear medicine, conventional x-ray, etc. The image from these modalities would then be used to assign dielectric constants to the various tissue types. For example, the following dielectric constants could be used as initial estimates for their corresponding tissues if the frequency is set at 915 MHz:

TABLE I

| Material | Material Properties | | |
|---|---|---|---|
| | $\epsilon_r'$ | $\epsilon_r''$ | Loss (dB/inch) |
| Water | 81 | 12 | 2.8 |
| Sea Water | Conductivity = 4 mho/m | | 20.06 |
| Tumor | 49 | 20 | 5.9 |
| Muscle | 50 | 25 | 7.3 |
| | 49 | 16 | 4.8 |
| | 58 | 19 | 5.2 |
| Fat | 6 | 2.2 | 1.9 |
| | 4.5 | 1.2 | 1.2 |
| | 8.4 | 1.6 | 1.2 |
| Bone | 6. | 1.0 | 0.9 |
| | 4.5 | 1.2 | 1.2 |
| | 8.4 | 1.6 | 1.2 |
| Gray Matter | 46 | 19 | 5.8 |

TABLE I-continued

| Material | Material Properties | | Loss (dB/inch) |
|---|---|---|---|
| | $\epsilon_r'$ | $\epsilon_r''$ | |
| White Matter | 32 | 8.9 | 3.3 |
| Blood | 58 | 15.6 | 4.3 |

The input of such a reference image is shown on console 122 in FIG. 1.

The computer 120 begins by setting the electric and magnetic fields throughout the region to zero in step 302. Then the computer 120 increments the time and the excitation of each element to be used as a source at step 304.

Figure 2:
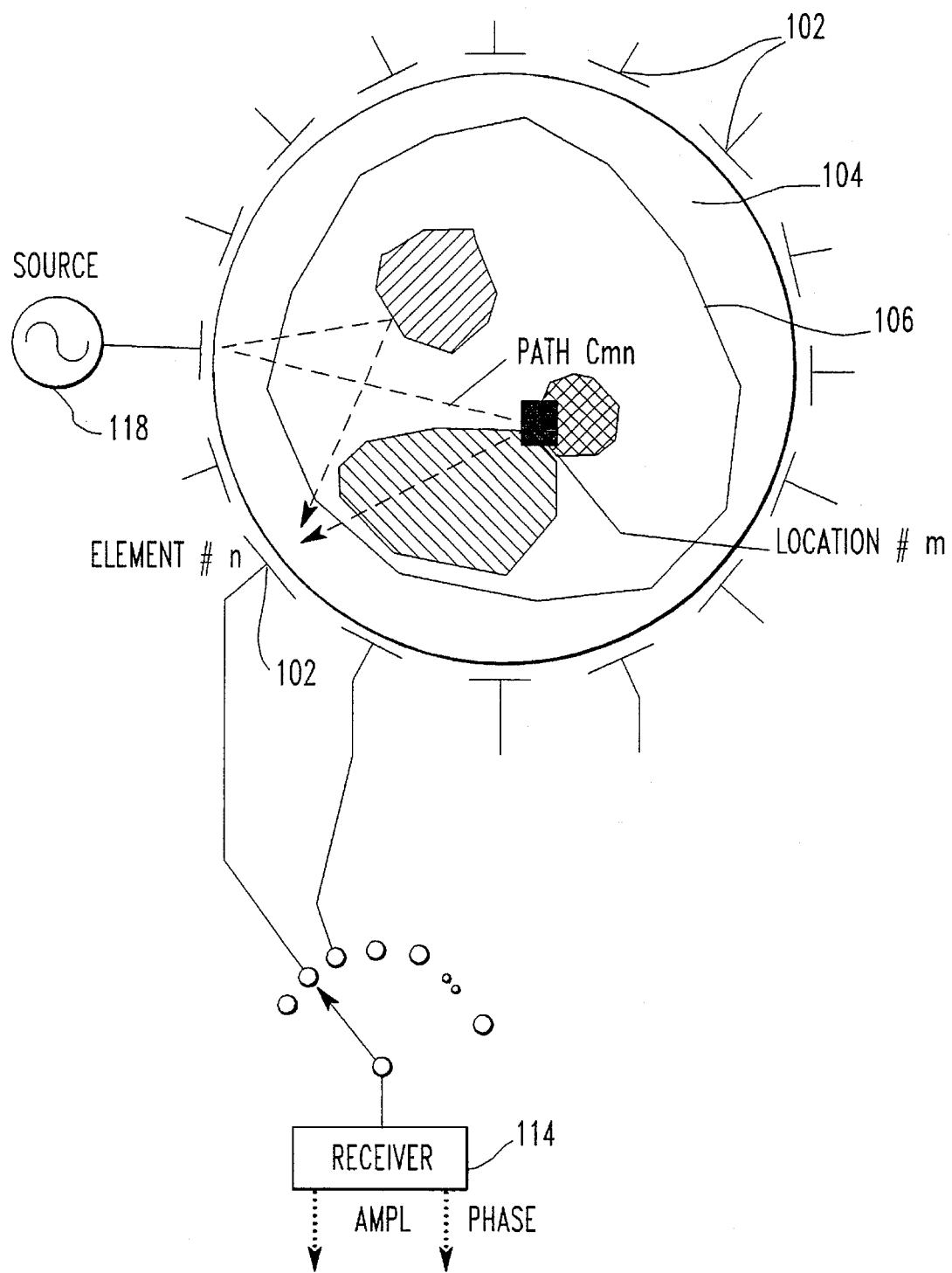
FIG. 2 schematically illustrates one element of an embodiment of the present invention.

At step 308, the computer 120 solves Maxwell's divergence equation for all x, y, and z at the incremented time and excitation, applying a time increment in electric field proportional to the spacial divergence in magnetic field and vice versa. This propagates a wave throughout the region, which eventually stabilizes to a sinusoidal time variation. At step 310, the computer 120 determines whether the fields within the area of interest 106 are stable for that time and excitation. If not, the time and the excitation of the signal from each source are incremented at step 304. The computer 120 continues this cycle until the fields are uniform and stable but oscillatory at each point. The computer 120 then stores the fields including the maximum amplitude value and the corresponding phase for each element 102. At step 316 the computer 120 determines whether the input signal from each of the elements 102 has been completed. If not, the time and excitation are incremented at step 304 and the cycle continues until each element has in fact completed at least a single pulse and the fields are stable. Once the fields are stable and the pulse is complete, the computer 120 then determines the maximum amplitude and correct phase and outputs the correct coupling values for the input signal at step 320. The reason for controlling the amplitude input at each element 102 can be seen in FIG. 2. While one would want the maximum amplitude from each element 102 that could be tolerated by the skin surface at that element, signals from source 118 can be reflected from the inhomogeneities in the area of interest 106. Therefore, the maximum amplitude that the skin may be subjected to at one element may be higher than the amplitude at another element. This is especially true if there are a lot of different tissue types with dissimilar dielectric constants in the area. At step 318, the computer 120 also determines the impedance for each radiator as a further measure of tissue characteristics.

As a first run, this procedure would then give you the initial computed coupling values. Those values are then input at step 404, as shown in FIG. 4, to be compared with measured values as a step in determining the correct amplitudes and phases for each element to heat the area of interest 106.

The apparatus 100 is used to send signals from each of the elements to get the measured coupling values that are used at step 402.

At step 405, the computer 120 then determines the error in the measured values and the initial coupling values. If at step 406 the error exceeds a predetermined value, then the computer 120 varies $\epsilon_r'$ and $\epsilon_r''$ in the area of interest at step 408 and redetermines the coupling values at step 410. The computer 120 then, based upon the variation determines optimum values of $\Delta\epsilon_r'$ and $\Delta\epsilon_r''$ at step 412. The computer 120 then determines new coupling values at step 414, as described above in relation to FIG. 3, which results in computed coupling values which are input at step 416. The computer 120 again determines whether the difference in these calculated signals and the measured signals is less than the predetermined value at step 405. This cycle continues until the difference at step 406 is determined to be less than the predetermined threshold value. At that point in time, the dielectric coefficients for the area of interest 106 are known and the computer 120 prompts the operator to input the target coordinates at step 418. The computer 120 then determines the appropriate phasing and amplitude values at step 420 to maximize the heating at the input coordinates. Those values are output at step 422 to the amplitude and phase driver 124.

Figure 4:
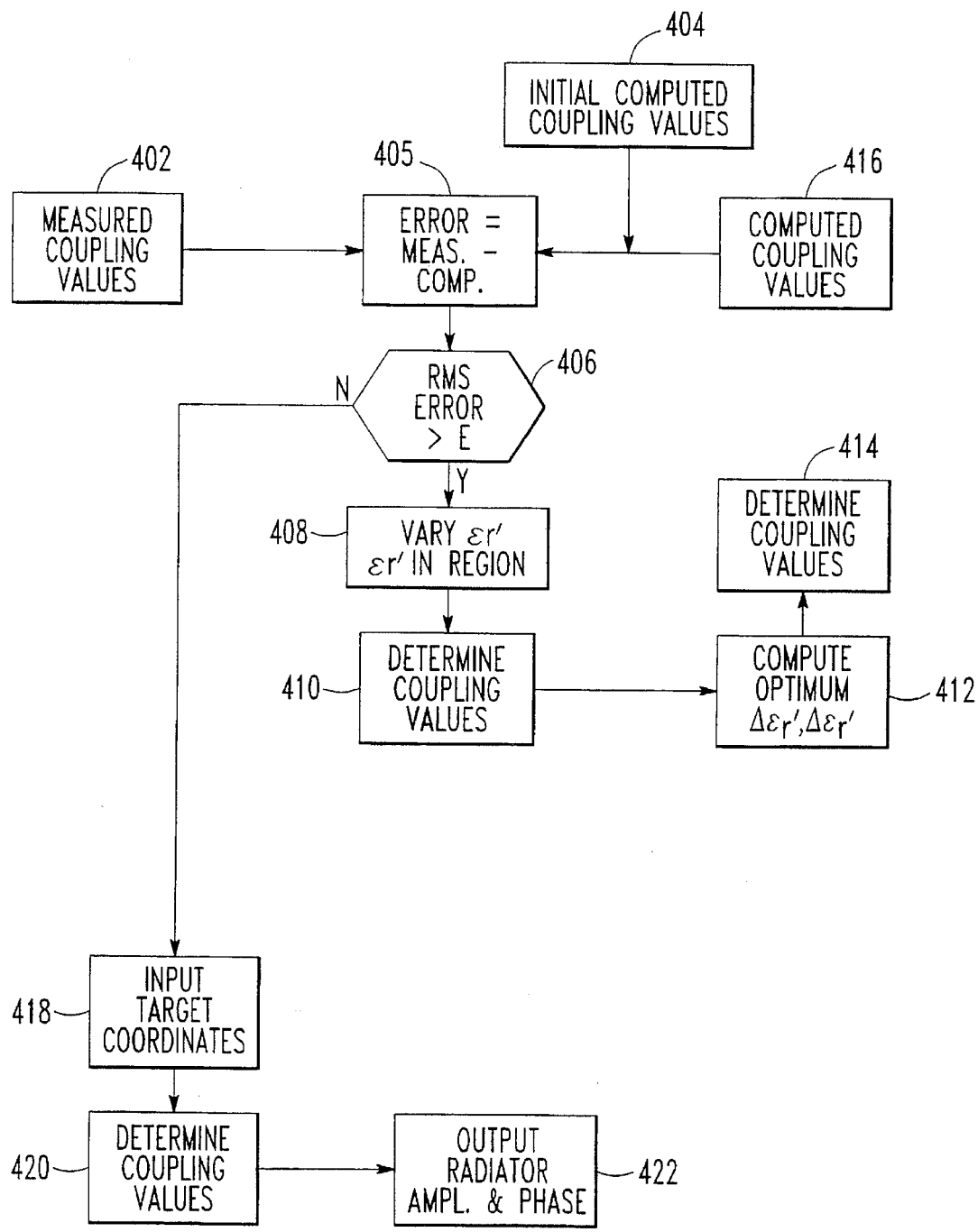
FIG. 4 is a flow chart illustrating the determination of amplitude and phases for the array elements.
Figure 5:
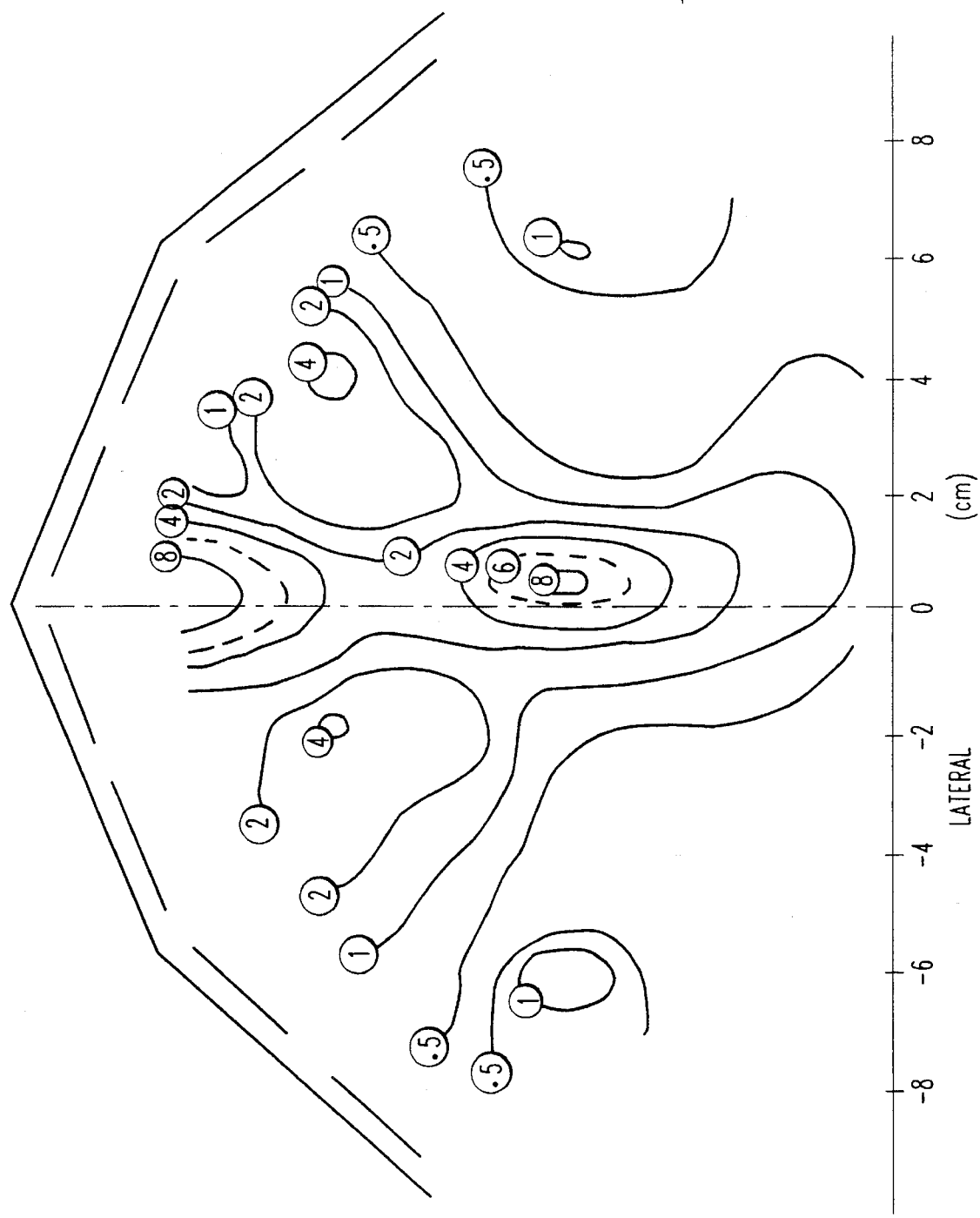
FIG. 5 illustrates the relative power densities according to one embodiment of the present invention.
Figure 6:
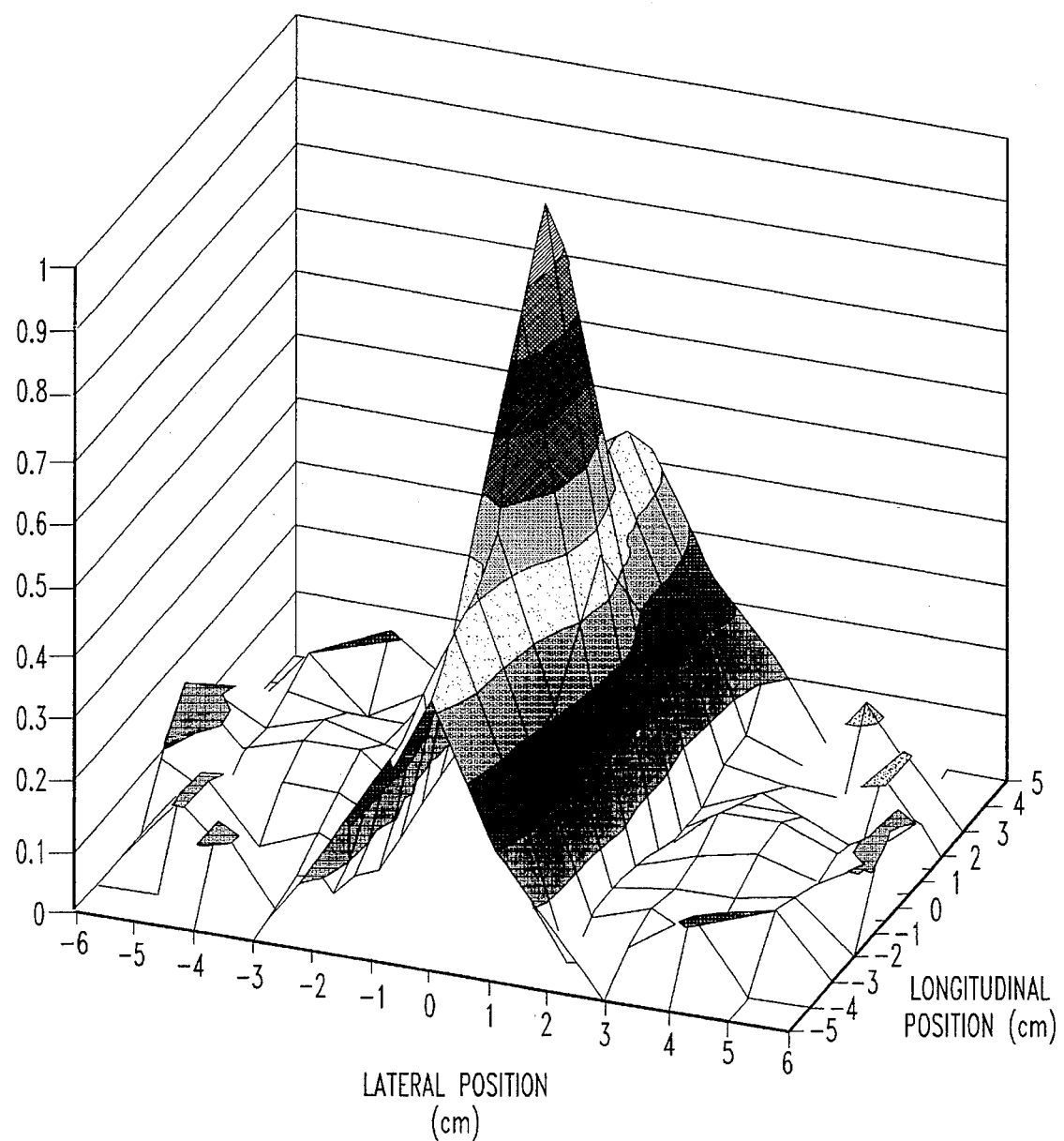
FIG. 6 illustrates the power density for a cylindrical embodiment of the present invention.
Figure 7:
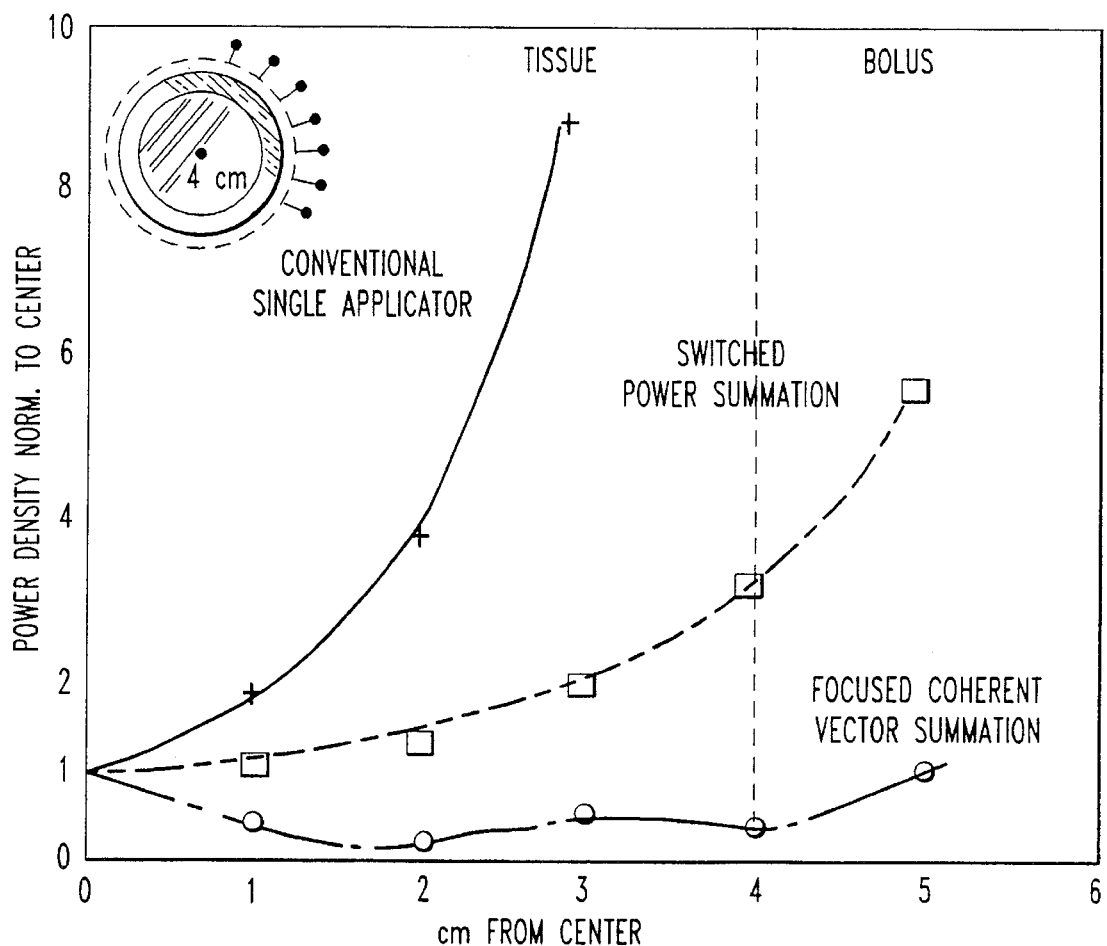
FIG. 7 illustrates power concentration at an area of interest according to an embodiment of the present invention.

The determination at step 420 in FIG. 4 can be done in two ways. In the first way, computer 120 determines the appropriate phase and amplitudes for each element 102 to give the maximum energy deposition at the target coordinates in the volume of tissue 108. This determination is made without regard to the total energy deposition in other tissues. Naturally, because the elements are focused on the volume of tissue 108, the highest energy deposition will be at the target coordinates. See, for example, FIGS. 5 and 6. However, that does not guarantee that the surrounding tissues are not receiving substantial energy and, therefore, are increasing in temperature as well. For example, it is well known in the microwave art, that while the signal can be high at the target location, the large, uncontrolled reflections can also create regions having high signals elsewhere in the treated body. Therefore, to determine appropriate amplitudes and phases, an output signal from each element is estimated for a signal generated from the approximate center. The output signal is used to determine the initial amplitudes and phases for signals from each element necessary to focus maximum energy at the approximate center of the area of interest. Thereafter, points within the area of interest where the energy from the signals is at a maximum are determined, and the appropriate amplitude and phase for each element is determined in order to maximize the ratio of energy at the approximate center to the energy at the determined points.

Alternatively, the estimated output signal is used to determine the electrical loss and phase from the approximate center to each of the elements and thereafter invert the signals to determine the appropriate amplitudes and phases to thereby maximize power deposition at the approximate center.

The second way, while more complicated, reduces this heating of other tissues. Computer 120 determines the maximum energy input at the target coordinates as well as all other points in the area of interest. The computer 120 then varies the amplitude and phase values of each element 102 to maximize the ratio of energy input at the target coordinates, to the largest energy input in the area of interest 106. This determination allows for maximum heating at the target coordinates while the heating of the surrounding tissue is kept to a minimum. This second method is more time consuming, and may not be needed depending on the tissue type and the amount of heat needed for treatment of the tissue.

Then computer 120, through amplitude and phase driver 124, applies the correct phases and amplitudes for each element 102 to phasers 112 and all elements 102 are set, via switches 110, to radiate. The source 118 is then set to radiate.

At any time after the heating of the volume of tissue 108 has commenced, source 118 should be set back to image so an image of the area of interest 106 can be made. The subsequent imaging, performed in the same manner as described above for the initial image, may be done either manually or automatically by computer 120. These subsequent images are formed rapidly since the errors are slight. The subsequent images are then subtracted from the initial image to get a subtracted image of the area of interest 106. This subtracted image would show an increase in temperature in the area of interest on console 122, because the dielectric constants of tissues vary rapidly with temperature, both in real and imaginary parts. Based upon the subtracted image, the operator can either continue to heat the volume of tissue, or if excessive heating has occurred elsewhere (perhaps because the simplified first method was used), adjust the phases and amplitudes of the phasers to ensure heating of only the desired volume of tissue 108.

It will be apparent to those skilled in the art that various modifications and variations can be made in the apparatus and method of the present invention without departing from the spirit or scope of the invention. Thus, it is intended that the present invention cover the modifications and variations of this invention provided they come within the scope of the appended claims and their equivalents.

I claim:

1. A method for noninvasively locating and heating a volume of tissue in a patient comprising the steps of:

placing a bolus in contact with the patient and substantially around an area of interest, said area of interest including said volume of tissue;

placing an array of antennas on said bolus and substantially around said area of interest, said array including a plurality of elements, each one of said elements being independently operable and each having the ability to send and receive signals;

selectively energizing at least one element of said array to send signals;

selectively energizing at least one other element of said array to receive said signals;

determining dielectric constants at a plurality of locations in said area of interest to obtain a configuration of measured dielectric constants from said received signals;

generating an initial image based upon said configuration of said measured dielectric constants;

selecting an approximate center of said volume of tissue on said initial image;

determining appropriate amplitudes and phases for each one of said plurality of elements of said array in accordance with the configuration of measured dielectric constants; and energizing each element of said array at respective appropriate amplitudes and phases to focus energy in said approximate center of said volume of tissue to preferentially heat said volume of tissue.

2. The method for noninvasively locating and heating a volume of tissue of claim 1 further comprising the steps of:

repetitively imaging said area of interest to create at least one subsequent image; and subtracting said initial image from said at least one subsequent image to determine temperature changes in said area of interest, said temperature changes being determined from changes in the dielectric constants of tissues in said area of interest.

3. The method of claim 2, wherein the step of determining dielectric constants comprises the substeps of:

estimating dielectric constants for said plurality of locations in said area of interest to obtain a configuration of estimated dielectric constants for said area of interest;

estimating an output signal from each of said plurality of elements for a signal generated from each element based upon the configuration of estimated dielectric constants, said estimated output signal having an amplitude and a phase;

generating a signal successively from each one of said elements, said signal having an amplitude and a phase;

receiving said successively generated signals at all other elements;

comparing said received signals to each corresponding estimated signal;

determining whether the differences between the amplitude and phase of the received signal and the amplitude and phase of the corresponding estimated signal exceed predetermined values at each element; and repetitively varying said configuration of estimated dielectric constants in response to said difference and estimating an output signal from each element until the difference between the amplitudes of the received signal and estimated signal does not exceed said predetermined value.

4. The method of claim 3, wherein the step of estimating the configuration of estimated dielectric constants comprises the substeps of:

imaging the area of interest using a modality that represents tissue types in said area of interest;

approximating a dielectric constant for each tissue type based upon known dielectric values for various tissue types; and coordinating said known dielectric values to said tissue type in said area of interest.

5. The method of claim 2, wherein the step of determining appropriate amplitudes and phases comprises the substeps of:

estimating an output signal from each of said plurality of elements for a signal generated from said approximate center;

determining initial amplitudes and phases for signals from each element of said array in accordance with said estimated output signal to focus maximum energy at said approximate center;

determining the points in said area of interest where energy from said signals is at a maximum; and determining the appropriate amplitude and phases for each element to maximize the ratio of energy at said approximate center to said determined points for said area of interest.

6. The method of claim 2, wherein the step of determining appropriate amplitudes and phases comprises the substeps of:

estimating an output signal from each of said plurality of elements for a signal generated from said approximate center;

determining the electrical loss and phase from said approximate center to each of said elements; and inverting said signals to determine the appropriate amplitudes and phases to maximize power deposition at said approximate center.

7. A method for noninvasively locating and heating a volume of tissue in a patient comprising the steps of:

placing a bolus in contact with the patient and placing an array of antennas on the bolus, said bolus and array substantially surrounding an area of interest, said area of interest including said volume of tissue and said array including a plurality of elements, each one of said elements being independently operable and each having the ability to send and receive signals at a plurality of frequencies;

selectively energizing at least one element of said array to send signals at a frequency greater than 800 MHz;

selectively energizing at least one other element of said array to receive said signals;

determining dielectric constants at a plurality of locations in said area of interest to obtain a configuration of measured dielectric constants from said received signals;

generating an initial image based upon said configuration of said measured dielectric constants;

selecting an approximate center of said volume of tissue on said initial image;

determining appropriate amplitudes and phases for each one of said plurality of elements of said array in accordance with the configuration of measured dielectric constants;

energizing each element of said array at respective appropriate amplitudes and phases at a frequency less than 1000 MHz to focus energy in said approximate center of said volume of tissue, thereby preferentially heating said volume of tissue;

repetitively imaging said area of interest at a frequency greater than 800 MHz to create at least one subsequent image; and subtracting said initial image from said at least one subsequent image to determine temperature changes in said area of interest, said temperature changes being determined from changes in the dielectric constants of tissues in said area of interest.

8. An apparatus for noninvasively locating and heating a volume of tissue in a patient comprising:

a bolus, said bolus for contacting the patient and substantially surrounding an area of interest when contacting the patient, said area of interest including said volume of tissue;

an array of antennas, said array being on said bolus and substantially surrounding said area of interest when said bolus is contacting the patient, said array including a plurality of elements, each one of said elements being independently operable and each having the ability to send and receive signals;

means for selectively energizing at least one element of said array to send signals;

means for selectively energizing at least one other element of said array to receive said signals;

means for determining dielectric constants at a plurality of locations in said area of interest when said bolus is contacting the patient to thereby obtain a configuration of measured dielectric constants from said received signals;

means for generating an initial image based upon said configuration of said measured dielectric constants;

means for selecting an approximate center of said volume of tissue on said initial image;

means for determining appropriate amplitudes and phases for each one of said plurality of elements of said array in accordance with the configuration of measured dielectric constants; and means for energizing each element of said array at respective appropriate amplitudes and phases to focus energy in said approximate center of said volume of tissue to preferentially heat said volume of tissue when said bolus is contacting the patient.

9. The apparatus for noninvasively locating and heating a volume of tissue in claim 8, further comprising:

means for repetitively imaging said area of interest when said bolus is contacting the patient to thereby create at least one subsequent image; and means for subtracting said initial image from said at least one subsequent image to determine temperature changes in said area of interest, said temperature changes being determined from changes in the dielectric constants of tissues in said area of interest.

10. The apparatus of claim 9, wherein said means for determining measured dielectric constants further comprises:

means for estimating a configuration of estimated dielectric constants for said area of interest;

means for estimating an output signal from each of said plurality of elements for a signal generated from each element based upon the configuration of estimated dielectric constants, each estimated signal having an amplitude and phase;

means for generating a signal successively from each one of said elements, each signal having an amplitude and phase;

means for receiving said successively generated signals at all other elements;

means for comparing said received signals to each corresponding estimated signal;

means for determining whether the difference between the amplitude and phase of the received signal and the corresponding estimated signal exceed predetermined values at each element; and means for repetitively varying said configuration of estimated dielectric constants in response to said difference and estimating the output signal from each element until the difference between the amplitude and phase of the received signal and estimated signal does not exceed said predetermined value.

11. The apparatus of claim 10, wherein said means for estimating the configuration of estimated dielectric constants further comprises:

means for imaging the area of interest using a modality that represents tissue types in said area of interest;

means for approximating a dielectric constant for each tissue type based upon known dielectric values for various tissue types; and means for coordinating said known dielectric values to said tissue type in said area of interest.

12. The apparatus of claim 10, wherein said means for determining appropriate amplitudes and phases further comprises:

means for estimating an output signal from each of said plurality of elements for a signal generated from said approximate center;

means for determining initial amplitudes and phases for signals from each element of said array in accordance with said estimated output signal to focus maximum energy at said approximate center;

means for determining the points in said area of interest where energy from said signals is at a maximum; and means for determining the appropriate amplitude and phases for each element to maximize the ratio of energy at said approximate center to said determined points for said area of interest.

13. The apparatus of claim 10, wherein said means for determining appropriate amplitudes and phases further comprises:

means for estimating an output signal from each of said plurality of elements for a signal generated from said approximate center;

means for determining the electrical loss and phase from said approximate center to each of said elements; and means for inverting said signals to determine the appropriate amplitudes and phases to maximize power deposition at said approximate center.

14. An apparatus for noninvasively locating and heating a volume of tissue in a patient comprising:

a bolus and an array of antennas, said bolus for contacting the patient and said array being on said bolus, said bolus and array substantially surrounding an area of interest when said bolus is contacting the patient, said area of interest including said volume of tissue and said array including a plurality of elements, each one of said elements being independently operable and each having the ability to send and receive signals at a plurality of frequencies;

means for selectively energizing at least one element of said array to send signals at a frequency greater than 800 MHz;

means for selectively energizing at least one other element of said array to receive said signals;

means for determining dielectric constants at a plurality of locations in said area of interest when said bolus is contacting the patient to thereby obtain a configuration of measured dielectric constants from said received signals;

means for generating an initial image based upon said configuration of said measured dielectric constants;

means for selecting an approximate center of said volume of tissue on said initial image;

means for determining appropriate amplitudes and phases for each one of said plurality of elements of said array in accordance with the configuration of measured dielectric constants;

means for energizing each element of said array at respective appropriate amplitudes and phases at a frequency less than 1000 MHz to focus energy in said approximate center of said volume of tissue when said bolus is contacting the patient, thereby preferentially heating said volume of tissue;

means for repetitively imaging said area of interest at a frequency greater than 800 MHz when said bolus is contacting the patient to thereby create at least one subsequent image; and means for subtracting said initial image from said at least one subsequent image to determine temperature changes in said area of interest, said temperature changes being determined from changes in the dielectric constants of tissues in said area of interest.

15. An apparatus for noninvasively heating a volume of tissue in a patient comprising:

an antenna array having multiple antenna elements for sending and receiving signals, said antenna array capable of substantially surrounding a selected area of the patient;

means for controlling said antenna array whereby selected antenna elements transmit signals and selected antenna elements receive said signals when said antenna array is substantially surrounding the selected area of the patient;

means for measuring the dielectric constant of a plurality of locations in said selected area of the patient based upon said received signals;

means for calculating the amplitude and phase of signals from said antenna elements to focus signals from said antenna elements on a volume of tissue within said selected area, where the calculation is based on the measured dielectric constants; and means for energizing said antenna elements whereby said volume of tissue is heated when said antenna elements substantially surround said selected area of the patient and transmit signals having the calculated amplitudes and phases.

16. The apparatus of claim 15 further comprising means for imaging said selected area based on the calculated dielectric constants.

* * * * *